United States Patent
Van Saarloos

(10) Patent No.: US 7,922,330 B2
(45) Date of Patent: Apr. 12, 2011

(54) FAST RESPONSE EYE TRACKING

(75) Inventor: Paul Philip Van Saarloos, Gwelup (AU)

(73) Assignee: Customvis PLC, Balcatta (AU)

( * ) Notice: Subject to any disclaimer, the term of this patent is extended or adjusted under 35 U.S.C. 154(b) by 259 days.

(21) Appl. No.: 11/913,956

(22) PCT Filed: May 15, 2006

(86) PCT No.: PCT/AU2006/000639
§ 371 (c)(1),
(2), (4) Date: Nov. 9, 2007

(87) PCT Pub. No.: WO2006/119584
PCT Pub. Date: Nov. 16, 2006

(65) Prior Publication Data
US 2008/0204658 A1    Aug. 28, 2008

(30) Foreign Application Priority Data
May 13, 2005    (AU) ................... 2005902455

(51) Int. Cl.
*A61B 3/14*    (2006.01)
*A61B 3/00*    (2006.01)
(52) U.S. Cl. .......................... 351/210; 351/246
(58) Field of Classification Search ........... 351/210–246
See application file for complete search history.

(56) References Cited

U.S. PATENT DOCUMENTS

| 4,812,033 A | 3/1989 | Ishikawa |
| 5,345,281 A | 9/1994 | Taboada et al. |
| 5,865,832 A | 2/1999 | Knopp et al. |

(Continued)

FOREIGN PATENT DOCUMENTS

JP    11271820    10/1999

(Continued)

OTHER PUBLICATIONS

International Search Report for International Application No. PCT/AU2006/000639.

(Continued)

*Primary Examiner* — Ricky L Mack
*Assistant Examiner* — Tuyen Q Tra
(74) *Attorney, Agent, or Firm* — Andrus, Sceales, Starke & Sawall, LLP

(57) ABSTRACT

An apparatus (10) for monitoring the position of an eye during a laser ablation treatment of the eye is provided. The apparatus includes optic means (110) for directing an incident light beam (102) along an optical path (104) onto the external surface of the eye (35) so as to illuminate a region of said surface that includes a segment of the limbus of the eye, and for directing back along said optical path (104), a return beam (122) comprising light of said incident beam scattered by said surface region; beam separation means (125) for separating the return beam (122) from the incident beam (102). The apparatus also includes at least one detector (120), having one or more detector segments (120a, 120b), for detecting said return beam (122), said detector segment(s) (120a, 120b) recording first and second values for light scattered respectively by the sclera and iris in said illuminated region. Movement of said limbal segment, and therefore of the eye (35), produces a change in at least one of said first and second values allowing such movement of the eye (35) to be monitored. A method corresponding to the apparatus is also disclosed.

20 Claims, 2 Drawing Sheets

U.S. PATENT DOCUMENTS

| | | |
|---|---|---|
| 5,966,197 A | 10/1999 | Yee |
| 5,980,513 A | 11/1999 | Frey et al. |
| 6,002,697 A | 12/1999 | Govorkov et al. |
| 6,095,648 A | 8/2000 | Birngruber et al. |
| 6,179,422 B1 | 1/2001 | Lai |
| 6,299,307 B1 | 10/2001 | Oltean et al. |
| 6,604,825 B2 | 8/2003 | Lai et al. |
| 6,614,584 B1 | 9/2003 | Govorkov et al. |
| 6,702,809 B1 | 3/2004 | Knopp et al. |
| 6,854,847 B2 * | 2/2005 | Lai et al. .................. 351/210 |
| 2002/0013575 A1 | 1/2002 | Lai et al. |
| 2003/0118217 A1 | 6/2003 | Kondo et al. |
| 2005/0024586 A1 | 2/2005 | Teiwes et al. |

FOREIGN PATENT DOCUMENTS

| | | |
|---|---|---|
| WO | WO 95/28879 | 11/1995 |
| WO | WO 99/23936 | 5/1999 |
| WO | 0027273 | 5/2000 |
| WO | 0157590 | 8/2001 |
| WO | 0233484 | 4/2002 |

OTHER PUBLICATIONS

Written Opinion of the International Searching Authority for International Application No. PCT/AU2006/000239.

* cited by examiner

FAST RESPONSE EYE TRACKING

FIELD OF THE INVENTION

This invention relates generally to the determination of the position of the eye during ophthalmic procedures, and is particularly useful for fixing and tracking eye position during ophthalmic surgery by laser ablation, which is most commonly carried out for refractive correction purposes.

BACKGROUND OF THE INVENTION

Refractive correction by laser ablation has evolved into a highly customised procedure in which an accurate topographical aberration map of the patient's eye is obtained, eg. using wavefront techniques, and a precision ablation profile pre-determined to a high degree of dimensional accuracy. The ablation profile is carried out by programming the laser surgical machine to apply multiple successive laser pulses with great precision to the corneal area being treated. The pulses may be of smaller uniform cross-section but scanned over controlled ablation patterns, or of larger cross-section but masked to varying cross-sections, with or without scanning.

Whichever ablation procedure is adopted, there is a requirement that the position of the eye be known initially with great accuracy, and that, during the procedure, any movements of the eye be accurately compensated for in the aiming of the laser pulses. It will be appreciated that patients are awake during the procedure and that movements that may arise include both voluntary and involuntary movements of the eye, and head movements: any of these movements can occur even when, as is normally the case, the patient is holding a steady gaze on a fixation target. Total immobilisation of the eye is not considered practical.

The conventional approach to eye tracking during ophthalmic surgery by ablation has been to focus on the pupil as an object readily detectable in an image or from reflection patterns, and to determine and track the location of the pupil's centre. Examples of this approach are provided by U.S. Pat. Nos. 5,345,281 and 5,980,513, and by international patent publication WO 00/27273, which also cites other references reliant on a pupil-based technique. U.S. Pat. No. 5,980,513 describes a system in which the treatment laser optics are employed to project an infrared sensor beam in multiple spots onto the pupil boundary, and to recover the reflected beam.

It is well recognised that a pupil varies in size with ambient light and other influences, and this is addressed by artificial dilation or by making allowance in the pattern recognition algorithms. However, what is not so well recognised is that the geometrical or mathematical centre of the pupil actually moves by up to 0.7 mm as the pupil expands and contracts in size. These shifts in the pupil centre may have been tolerable in conventional "broad-scale" ablations but are wholly unacceptable in high precision custom ablations. Pupil-based eye tracking is also adversely affected in surgical situations by the fluid changes that occur adjacent the pupil: the required drier environs diminishes the clarity of the pupil boundary.

The present applicant considers that the better reference point for accurate eye tracking is the limbus, the boundary between the iris and the sclera regions, because the limbus maintains a fixed relationship and a close circularity with respect to the lens of the cornea, which is of course the object of the ablation. There have been a number of patents that propose limbus-based eye tracking or position detection, including U.S. Pat. Nos. 5,865,832, 5,966,197, 6,095,648, 6,179,422, 6,299,307, 6,604,825, and 6,702,809, and US patent publication 2002/0013575. These arrangements typically involve detection of an intensity difference between light reflected from the sclera, which is of course white, and the iris, which is coloured.

It is not to be inferred that, by referring to or discussing herein specifically identified documents by number, the applicant is suggesting that these documents constitute common general knowledge.

U.S. Pat. Nos. 5,865,832, 5,966,197, and 6,702,809 disclose eye tracking systems in which the limbus is statically illuminated by lateral light sources, and a lune-shaped image of the whole limbus is projected onto a multiple element detector system. The system of U.S. Pat. No. 5,966,197 employs pairs of detectors on a pair of mutually orthogonal diameters to detect the two limbus positions on each diameter, by monitoring spatially for steps on the detected image.

U.S. Pat. No. 6,179,422 employs a different approach: instead of static illumination of the whole limbus, an illuminating beam is scanned radially across a segment of the limbus, using the same scanning optics as for the ablation beam. The scattered beam is recovered by separate optics and directed to a photo-detector that monitors for an amplitude step indicative of the limbal boundary.

An emerging challenge for eye tracking systems in refraction correction surgery by laser ablation is to match the dynamic capabilities of the ablation process in terms of both responsive times and spatial accuracy. Pulse rates of 300 Hz are now being achieved, for which a tracking response rate of the order of 1 kilohertz is desirable. Higher response rates, e.g. tens of kilohertz, may be sought in future.

It is an object of the invention to provide improved methods for determining and/or tracking the position of an eye, that are capable of the response times and spatial accuracy required for modern ophthalmic laser ablation surgery.

SUMMARY OF THE INVENTION

The invention provides, in a first aspect, a method of monitoring the position of an eye during a laser ablation treatment of the eye, the method including:
   directing an incident light beam along an optical path onto the external surface of the eye so as to illuminate a region of said surface that includes a segment of the limbus of the eye;
   detecting, with at least one detector having one or more detector segments, a return beam comprising light of said incident beam scattered by said surface region, which return beam returns back along said optical path and is separated from the incident beam at beam separation means, said detector segment(s) recording first and second values for light scattered respectively by the sclera and iris in said illuminated region;
   whereby movement of said limbal segment, and therefore of the eye, produces a change in at least one of said values.

The invention also provides, in its first aspect, apparatus for monitoring the position of an eye during a laser ablation treatment of the eye, the apparatus including:
   optic means for directing an incident light beam along an optical path onto the external surface of the eye so as to illuminate a region of said surface that includes a segment of the limbus of the eye, and for directing back along said optical path, a return beam comprising light of said incident beam scattered by said surface region;
   beam separation means for separating the return beam from the incident beam; and
   at least one detector, having one or more detector segments, for detecting said return beam, said detector segment(s)

recording first and second values for light scattered respectively by the sclera and iris in said illuminated region;

whereby movement of said limbal segment, and therefore of the eye, produces a change in at least one of said values.

In a preferred arrangement, the at least one detector has plural detector segments which record said first and second values for light scattered respectively by the sclera and iris, and the detector segments are monitored for change in either or both values. Alternatively, said at least one detector has a single detector segment which records both of said first and second values for light scattered respectively by the sclera and iris and the detector segment is monitored for a change in the sum of the values.

Typically, said limbal segment extends substantially radially across the limbus.

Preferably, the incident and return beams are scanned over said region and/or limbus segment.

The method of the first aspect of the invention may be incorporated in a method of treating an eye by laser ablation, eg. for refractive correction purposes, in which the method of the invention is utilised to determine and/or track the position of the eye. Advantageously, the ablation is adjusted or modified responsive to the tracked eye position.

The apparatus of the first aspect of the invention advantageously forms part of ophthalmic laser ablation apparatus having:
  means to accommodate a patient in a position for performing a laser ablation procedure on an eye of the patient;
  means for directing a controlled laser beam onto said eye for performing said procedure;
  apparatus according to the first aspect of the invention for monitoring the position of an eye during a laser ablation treatment of the eye; and
  controller means for controlling said laser beam to perform said procedure, which means is responsive to said first and second values recorded by said detector segments.

In a second aspect, the invention provides apparatus for monitoring the position of an eye during a laser ablation treatment of the eye, the apparatus including:
  means to record an instantaneous image of a first region of the eye of the patient that traverses the limbus of the eye;
  means to analyse said image to derive a first indication of the location of the limbus in said first region at first intervals;
  first optic means for directing an incident beam along an optical path onto the external surface of the eye so as to illuminate a second region of said surface that includes a segment of the limbus of the eye, and for receiving a return beam comprising light of said incident beam scattered by said surface region;
  at least one detector, for detecting said return beam and for determining a second indication of the location of the limbus in said second region of said surface, at second intervals substantially shorter than the first intervals;
  means responsive to said first indication for accurately monitoring the position of the eye at said first or greater intervals, and to said second indication for updating that position within said first or greater intervals.

In its second aspect, the invention further provides a method of monitoring the position of an eye during a laser ablation treatment of the eye, the method including:
  recording an instantaneous image of a first region of the eye of the patient that traverses the limbus of the eye, and analysing said image to derive a first indication of the location of the limbus, in said first regions at first intervals;
  directing an incident beam along an optical path onto the external surface of the eye so as to illuminate a second region of said surface that includes a segment of the limbus of the eye;
  detecting a return beam comprising light of said incident beam scattered by said second region of said surface and determining a second indication of the location of the limbus in said second region of said surface, at second intervals substantially shorter than the first intervals; and
  responding to said first indication to accurately monitor the position of the eye at said first or greater intervals, and to said second indication to update that position within said first or greater intervals.

BRIEF DESCRIPTION OF THE DRAWINGS

The invention will be further described, by way of example only, with reference to the accompanying drawings, in which.

DETAILED DESCRIPTION OF THE EMBODIMENTS

Figure 1:
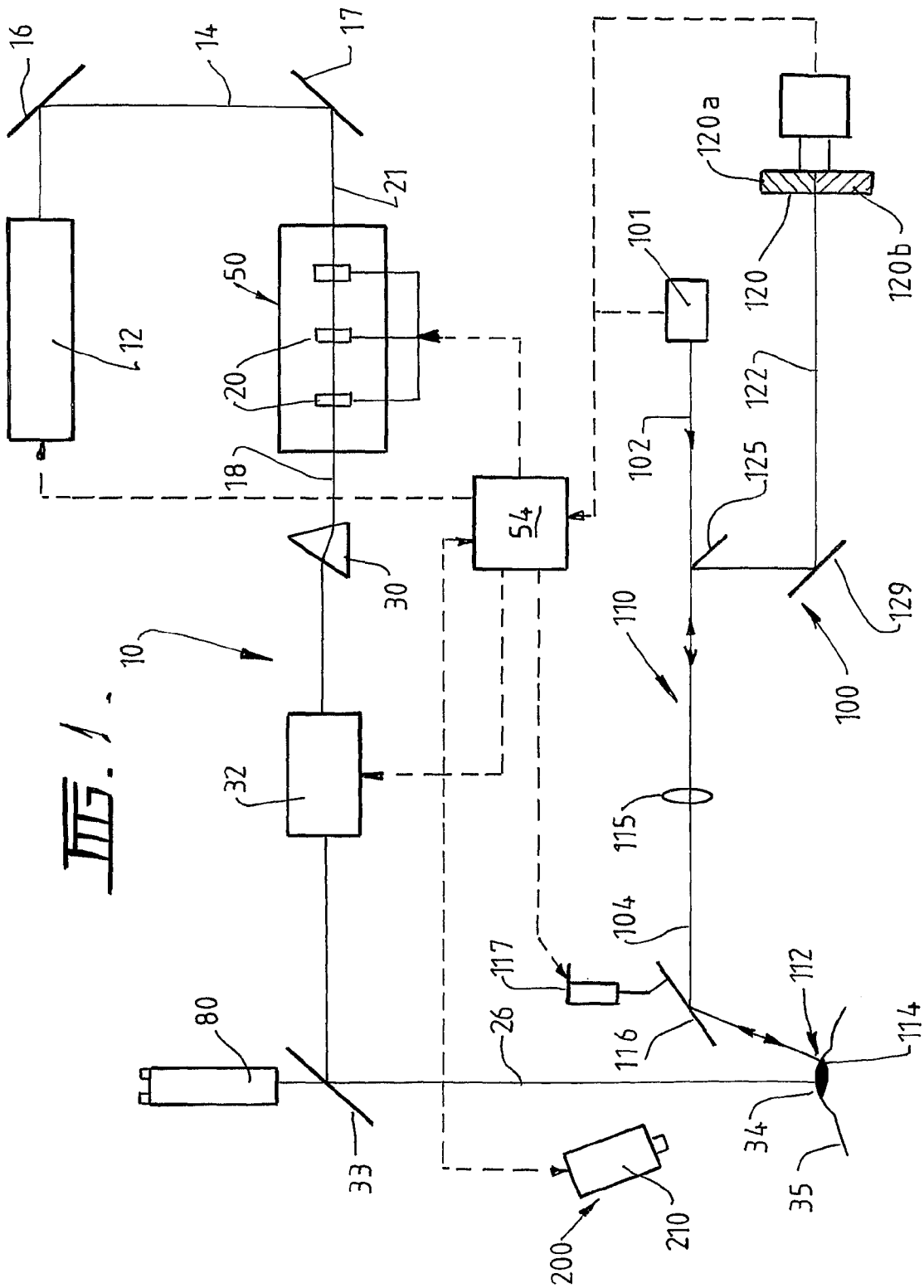
FIG. 1 is a highly schematic representation of certain components of an ophthalmic laser ablation apparatus that incorporates a solid state laser engine and is modified and programmed for carrying out the method of the invention.

A suitable apparatus 10 (FIG. 1) for carrying out laser ablation on a patient to effect refractive correction, includes a solid state laser 12 that emits a primary laser beam 14 in the infra-red region of the electromagnetic spectrum. Primary laser beam 14 is guided by optical elements, represented as mirrors 16, 17, along an optical alignment or axis 21, through a harmonic generation module 50 comprising a series of non-linear optical (NLO) crystals 20 from which emerges a multi-wavelength output beam 18. Beam 18 comprises the original beam 14 and several harmonics generated by crystals 20. The desired harmonic 26 is separated out by a prism 30, a dichroic mirror arrangement or other suitable means. Beam 26 is directed by a beam delivery scanner system 32 and further optics 33 onto the cornea 34 of an eye 35 of a supine patient accommodated on a bed (not shown) forming part of the system.

Controller 54, typically a computer system, controls at least the output beam parameters of laser 12, module 50 and the elements of the beam delivery system 32 so as to apply a customised ablation profile to each eye of the patient. A suitable microscope 80, focussed on the cornea, is provided to allow the surgeon to inspect and monitor the procedure.

A particularly suitable laser 12 is a Q-switched neodymium:YAG laser producing a 2-10 mm diameter pulsed laser beam 14 of fundamental wavelength 1064 nm. The beam 14 is collimated, resulting in a collimated harmonically generated beam downstream. A variety of other laser sources are suitable but preferred sources are $Nd^{3+}$ doped laser media such as Nd:YLF, Nd:glass and $Nd:YVO_4$.

In order to ensure that the ablation profile is delivered with precision to the corneal surface, controller 54 must know with precision the initial position of the eye and must track the position of the eye during the procedure: any detected displacement of the cornea must be reflected either by an adjustment of the ablation profile or by suspension of the ablation. The tracking is for the purpose of detecting any lateral movement of the eye, whether voluntary or involuntary on the part of the patient, and including movement arising from movement of the head.

The apparatus is fitted with two separate eye tracking sub-systems 100, 200, respectively producing an indication that is less accurate but a faster response on the one hand, and slow but more accurate on the other.

The first responsive sub-system 100, the fast response eye tracker, is typically but not essentially a pair of similar sub-systems, one for each of two orthogonal axes in the plane of the eye. It is proposed here to describe a single sub-system, but it is emphasised that there will usually be two. Each sub-system 100 comprises a secondary light source 101, a confocal optic system 110, and a plural-segment detector 120. Light source 101 is conveniently an ultra-bright white, yellow, green or blue LED, and outputs an incident beam 102 that is directed by optic system 110 along an optical path 104 onto the external surface of the eye so as to illuminate a region 112 of this surface that includes a segment 114 of the limbus of the eye.

Optic system 110 includes a focussing lens 115 and a scanning mirror 116 controlled by a piezo-electric actuator 117 for scanning beam 102 over the eye region of interest. A return beam 122, comprising light of incident beam 102 scattered by surface region 112, is returned along optical path 104 to a scraping mirror 125 that separates return beam 122 from the incident beam 102 to be focussed (by lens 115 and via optics represented by mirror 129) onto detector 120. In an alternative arrangement, element 125 might be a beamsplitter.

Figure 2:
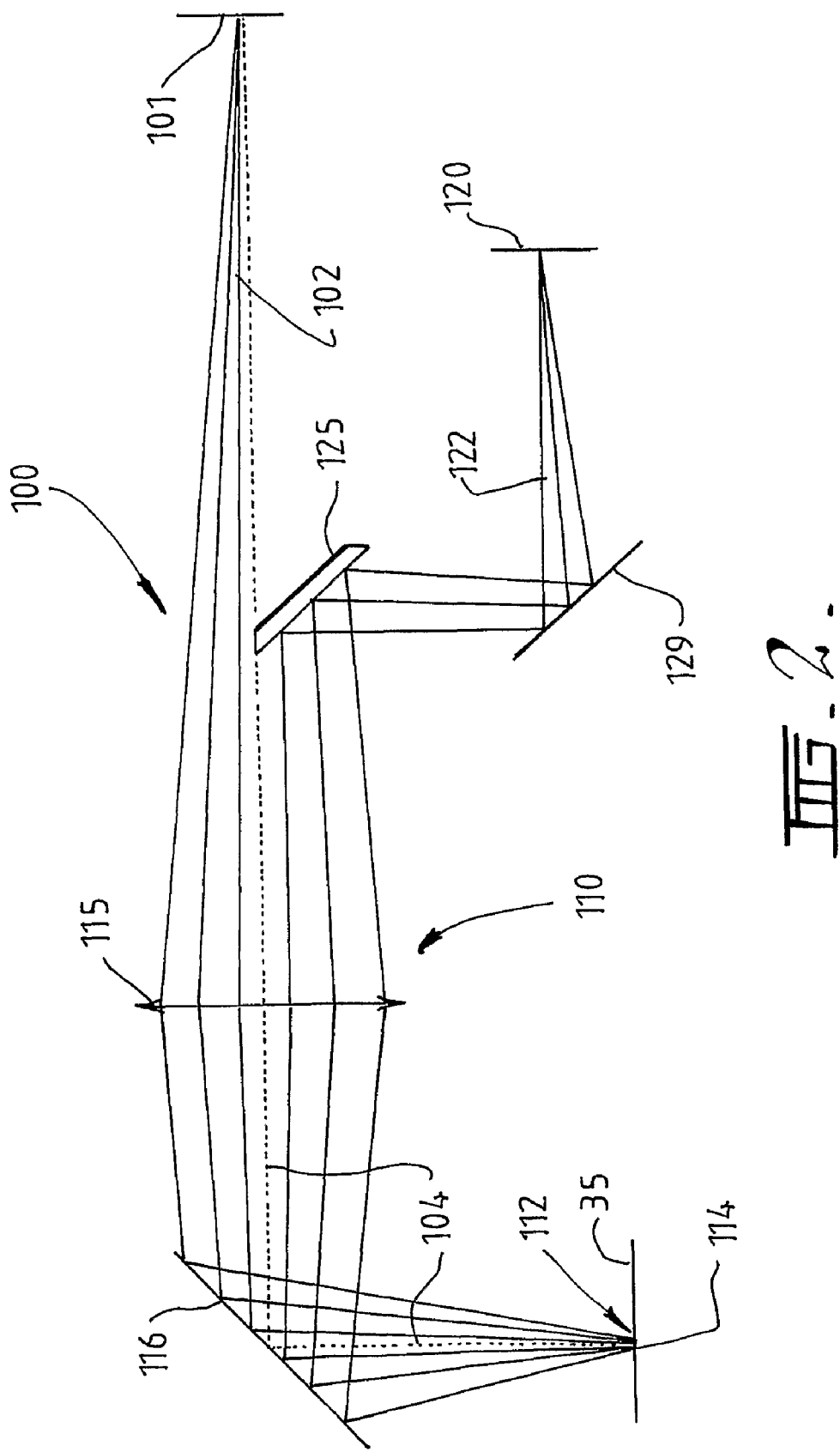
FIG. 2 is a ray diagram illustrating an element of the inventive concept.

As explained in the ray diagram of FIG. 2, one half of each of lens 115 and scanning mirror 116 transmits half of the incident beam 102, while the other half transmits the return beam 122 to scraping mirror 125 (which blocks the other half of incident beam 102). Thus, reference herein to the same optical path includes the illustrated arrangement in which the incident and return beams traverse complementary halves of the same optical components.

Detector 120 is a split photosensor having two detector segments 120a, 120b that, at an optimum neutral setting of the sub-system, respectively receive light scattered by the sclera and iris in region 112. Detector segments 120a, 120b record first and second values for light scattered by the sclera and iris in region 112.

A suitable form of detector 120 is a standard segmented photodiode detector or other detector, e.g. a CCD detector, that is spatially pixellated on its receiver interface.

It will be appreciated that any movement or variation of the limbal boundary from the ideal location—ie. where the "imaged" boundary in return beam 122 impinges the boundary between the detector segments 120a, 120b—will cause a detectable change in the output values recorded by the detector segments 120a, 120b. Since movement of the limbus or limbal boundary indicates movement of the eye, the detector output is highly and rapidly sensitive to any movement of the eye.

As the image of the limbus moves, say, to the iris, light from the iris will be shifted onto detector segment 120a. The net result is a decrease in the response from detector segment 120a. A similar increase in the response from detector segment 120b indicates a movement in the other direction.

Assuming uniform intensity of the iris side and of the sclera side, and a sharp transition between, the movement is given by:

$$du = \frac{L}{M} \times \frac{V_A - V_{A0} + V_B - V_{B0}}{V_{A0} - V_{B0}} \quad (1)$$

where du is the movement in the direction of detector segment 120a to detector segment 120b, L is the size of the detector and M is the optical magnification of the image. $V_A$ and $V_B$ are respectively the responses from detector segment 120a, 120b after the movement, and $V_{A0}$ and $V_{B0}$ are respectively the responses from detector segment 120a, 120b prior to the movement.

For any given L, M, $V_{A0}$ and $V_{B0}$, the root-mean-square error in du due to noise in $V_A$ and $V_B$ is $$\sigma_{du} = \frac{L}{M} \times \frac{\sqrt{2}\,\sigma_v}{|V_{A0} - V_{B0}|} \quad (2)$$

where $\sigma_v$ is the root-mean-square noise level in $V_A$ and $V_B$. Equation (2) specifies the required noise levels (including quantisation noise due to digitisation) in $V_A$ and $V_B$ to achieve a given error performance in du.

Now consider the situation where the image has moved to the extreme position where it lies only over the iris. In this case, $V_A = V_B = V_{B0}$ and $du = -L/M$. At the other extreme, $V_A = V_B = V_{A0}$ and $du = +L/M$. It follows that the maximum movement that can be quantified is $$|du_{max}| = \frac{L}{M}. \quad (3)$$

If the movement is greater than $du_{max}$, the sign of du still gives the direction of the movement.

If the limbus is recentred at time intervals of T by periodically adjusting the alignments of the optics, then the maximum velocity that can be quantified is $$|v_{max}| = \frac{|du_{max}|}{T} = \frac{L}{MT}. \quad (4)$$

In the event that the limbus image moves completely off the detector, both detector segments have the same response as the two above mentioned extremes. The direction of movement can be inferred from the intensity of the responses. If the limbus image is not properly focused onto the detectors, both detectors have the same response.

The light source 101 will be pulsed so that it can be distinguished from the various other light sources in the ablation system. The light intensity scattering off the surface of the patient's eye is detected using a low noise photo amplifier, a bandpass filter and an amplitude detector.

A minimum of two light-source/detector-pair systems are required to track eye movements in two dimensions. Ideally they will be positioned 90° apart around the limbus.

Because of the circular shape of the limbus, a movement in one axis (dy) will also register as a small movement in the orthogonal axis (dx). This can be corrected for by knowledge of the limbal shape, which can be determined for each patient.

Typically, a feedback loop is in place, managed by controller 54, in which the direction of beam 102 is adjusted until the limbus is re-centered at detector 120, by scanning mirror 116 of optic system 110. In this way, accurate coordinates for the eye's altered position can be rapidly determined. Controller 54 also responds appropriately in its management of ablation apparatus 10, eg. by suspending ablation or adjusting the direction of the beam 26.

By adopting the twin strategy of a confocal optical system and a plural segment detector, it is possible to achieve response times less than 1 msec with a high level of reliability and more than a match for an ablation repetition rate of 300 Hz. Any loss of scattered beam intensity arising from the optics of a confocal layout, especially at scraping mirror 125, relative to a dedicated return path, is not great enough to negate the benefit of eliminating uncertainties that arise from relative variations between two different optical paths. It will be appreciated that the position of the laser spot on the eye can be moved around by scanning mirror 116 without misaligning the detector 120.

For achieving high positional accuracy as well as a rapid response time, eye tracking sub-system 100 is complemented by and regularly calibrated or set by, eye tracking sub-system 200.

Sub-system 200 includes a miniature digital video camera 210, is positioned for recording a full image of sufficient of the eye to indicate the whole limbus and adjacent sclera, at predetermined intervals, eg. of the order of milliseconds. This camera is activated by, and delivers its digital recorded images to, the main controller 54 of the apparatus.

Controller 54 utilises appropriate image analysis techniques, of which there are a number known in the eye tracking art, for providing an accurate primary indication of limbus position, and therefore of eye position, at regular, relatively longer, intervals. This primary eye position indication is then updated at a relatively much faster response rate, i.e. at intervals within and much less than the aforementioned relatively longer intervals, by the eye position indication derived by sub-system 100, and is therefore also employed to determine the incidence zone of beam 102, initially and also by way of on-the-run adjustment.

In an alternative utilisation, sub-system 100 may be used passively: when eye movement is detected by it, ablation is suspended until sub-system 200 provides an accurate new position on which to base renewed ablation.

The invention claimed is:

1. An apparatus for monitoring the position of an eye during a laser ablation treatment of the eye, the apparatus including:
   an imaging sub-system to record an instantaneous image of a first region of the eye of the patient, which first region traverses the limbus of the eye and to analyze said image to derive a first indication of the location of the limbus in said first region at first intervals;
      first optics configured to direct an incident beam along an optical path onto the external surface of the eye so as to illuminate a second region of said surface, which second region includes a segment of the limbus of the eye, and to receive a return beam comprising light of said incident beam scattered by said second region; and
   at least one detector configured to detect said return beam and to determine a second indication of the location of the limbus in said second region of said surface, at second intervals, wherein the second intervals are substantially shorter than the first intervals;
   the apparatus being configured to determine in response to said first indication the position of the eye at said first or greater intervals, and in response to said second indication update that position within said first or greater intervals.

2. The apparatus of claim 1, wherein the at least one detector is configured to record respective first and second values for light scattered by the sclera and iris in the second region.

3. The apparatus of claim 2, wherein said at least one detector has respective detector segments to record said first and second values and configured to monitor for change in either or both values.

4. The apparatus of claim 3, wherein said second region extends substantially radially across the limbus.

5. The apparatus of claim 4, including a scanning arrangement to scan the incident and return beams over said region and/or limbus segment.

6. The apparatus of claim 2, wherein said at least one detector has a single detector segment which records both of said first and second values for light scattered respectively by the sclera and iris; wherein the at least one detector is configured to monitor for a change in the sum of the values.

7. The apparatus of claim 1, wherein said second region extends substantially radially across the limbus.

8. The apparatus of claim 1, including a scanning arrangement to scan the incident and return beams over said region and/or limbus segment.

9. The apparatus of claim 1, wherein the return beam returns back along the optical path and is separated from the incident beam at a beam separator.

10. A method of monitoring the position of an eye during a laser ablation treatment of the eye, the method including:
    recording an instantaneous image of a first region of the eye of the patient, which first region traverses the limbus of the eye;
    analyzing said image to derive a first indication of the location of the limbus, in said first regions at first intervals;
    directing an incident beam along an optical path onto the external surface of the eye so as to illuminate a second region of said surface that includes a segment of the limbus of the eye;
    detecting a return beam comprising light of said incident beam scattered by said second region of said surface and determining a second indication of the location of the limbus in said second region of said surface, at second intervals substantially shorter than the first intervals; and
    determining in response to said first indication to the position of the eye at said first or greater intervals; and
    updating the position of the eye within said first or greater intervals in response to said second indication.

11. The method of claim 10, wherein said determining said second indication includes monitoring respective first and second values for light scattered by the sclera and iris in the second region.

12. The method of claim 11, wherein said at least one detector has respective detector segments to record said first and second values, and said determining the second indication includes monitoring the detector segments for change in either or both of the first and second values.

13. The method of claim 12, wherein said second region extends substantially radially across the limbus.

14. The method of claim 13, wherein the incident and return beams are scanned over said second region and/or limbus segment.

15. A method of treating an eye by laser ablation, the method including determining and/or tracking the position of the eye by monitoring the position of the eye in accordance with the method of claim 14, and adjusting or modifying the ablation responsive to the tracked eye position.

16. The method of claim 11, including summing the first and second values; and monitoring for a change in the sum of the first and second values.

17. The method of claim 11, wherein the return beam returns back along the optical path and is separated from the incident beam at a beam separator.

18. The method of claim 10, wherein said segment second region extends substantially radially across the limbus.

19. The method of claim 10, wherein the incident and return beams are scanned over said second region and/or limbus segment.

20. A method of treating an eye by laser ablation, the method including determining and/or tracking the position of the eye by monitoring the position of the eye in accordance with the method of claim 10, and adjusting or modifying the ablation responsive to the tracked eye position.

* * * * *